(12) United States Patent
Nawana

(10) Patent No.: US 12,029,562 B2
(45) Date of Patent: Jul. 9, 2024

(54) DERMAL PATCH SYSTEM

(71) Applicant: Neoenta LLC, Weston, MA (US)

(72) Inventor: Namal Nawana, Weston, MA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 17/412,205

(22) Filed: Aug. 25, 2021

(65) Prior Publication Data

US 2022/0330860 A1   Oct. 20, 2022

Related U.S. Application Data

(60) Provisional application No. 63/190,700, filed on May 19, 2021, provisional application No. 63/174,956, filed on Apr. 14, 2021.

(51) Int. Cl.
*A61B 5/15* (2006.01)
*A61B 5/151* (2006.01)

(52) U.S. Cl.
CPC .. *A61B 5/150969* (2013.01); *A61B 5/150022* (2013.01); *A61B 5/150145* (2013.01); *A61B 5/150236* (2013.01); *A61B 5/151* (2013.01)

(58) Field of Classification Search
CPC ........ A61B 5/150969; A61B 5/150022; A61B 5/150145
See application file for complete search history.

(56) References Cited

U.S. PATENT DOCUMENTS

| | | |
|---|---|---|
| 5,015,228 A | 5/1991 | Columbus et al. |
| 5,338,308 A | 8/1994 | Wilk |
| 5,441,490 A | 8/1995 | Svedman |
| 5,527,288 A | 6/1996 | Gross et al. |
| 5,602,037 A | 2/1997 | Ostgaard et al. |
| 5,636,640 A | 6/1997 | Staehlin |
| 5,680,872 A | 10/1997 | Sesekura et al. |
| 5,848,991 A | 12/1998 | Gross et al. |
| 5,997,501 A | 12/1999 | Gross et al. |

(Continued)

FOREIGN PATENT DOCUMENTS

| | | |
|---|---|---|
| AU | 2006283345 A1 | 3/2007 |
| AU | 2016266112 A1 | 12/2016 |

(Continued)

OTHER PUBLICATIONS

English machine translation of JP-2004024164-A, patents.google.com, 8 pages.

(Continued)

*Primary Examiner* — Sean P Dougherty

(74) *Attorney, Agent, or Firm* — Potomac Law Group, PLLC; John J. Penny, Jr.

(57) ABSTRACT

A system for collecting a physiological sample includes a dermal patch configured for attaching to a subject's skin and an applicator for coupling to the dermal patch. The dermal patch includes a reservoir configured to store a processing fluid, a sample collection chamber for receiving the processing fluid and a physiological sample extracted from a subject. The applicator includes at least one actuating lever for activating the dermal patch to receive the physiological sample from the subject and directing the physiological sample into the sample collection chamber.

21 Claims, 10 Drawing Sheets

(56) References Cited

U.S. PATENT DOCUMENTS

| | | |
|---|---|---|
| 6,234,980 B1 | 5/2001 | Bell |
| 6,315,985 B1 | 11/2001 | Wu et al. |
| 6,454,140 B1 | 9/2002 | Jinks |
| 6,500,150 B1 | 12/2002 | Gross et al. |
| 6,506,168 B1 | 1/2003 | Fathallah et al. |
| 6,524,284 B1 | 2/2003 | Marshall |
| 6,610,273 B2 | 8/2003 | Wu et al. |
| 6,623,457 B1 | 9/2003 | Rosenberg |
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Astovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 | 12/2009 | Wall |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 | 8/2014 | Brancazio |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 | 7/2016 | Fletcher et al. |
| 9,380,973 B2 | 7/2016 | Fletcher et al. |
| 9,468,404 B2 | 10/2016 | Hayden |
| 9,480,428 B2 | 11/2016 | Colin et al. |
| 9,504,813 B2 | 11/2016 | Buss |
| 9,522,225 B2 | 12/2016 | Chong et al. |
| 9,549,700 B2 | 1/2017 | Fletcher et al. |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |
| 9,724,462 B2 | 8/2017 | Rotem |
| 9,730,624 B2 | 8/2017 | Gonzalez-Zugasti et al. |
| 9,770,578 B2 | 9/2017 | Chowdhury |
| 9,775,551 B2 | 10/2017 | Bernstein et al. |
| 9,782,574 B2 | 10/2017 | Simmers |
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |

(56) References Cited

U.S. PATENT DOCUMENTS

| | | |
|---|---|---|
| 10,010,706 B2 | 7/2018 | Gonzalez et al. |
| 10,010,707 B2 | 7/2018 | Colburn et al. |
| 10,016,315 B2 | 7/2018 | Letourneau et al. |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 | 3/2020 | Peeters et al. |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1* | 9/2022 | Nawana ............... A61B 5/157 |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 | 6/2002 | Lin et al. |
| 2002/0193740 A1 | 12/2002 | Alchas et al. |
| 2004/0002121 A1 | 1/2004 | Regan et al. |
| 2004/0010207 A1* | 1/2004 | Flaherty ............... A61B 5/157 |
| | | 600/573 |
| 2004/0059256 A1 | 3/2004 | Perez |
| 2004/0059366 A1 | 3/2004 | Sato et al. |
| 2004/0106904 A1 | 6/2004 | Gonnelli et al. |
| 2004/0162467 A1 | 8/2004 | Cook |
| 2005/0106713 A1 | 5/2005 | Phan et al. |
| 2005/0118388 A1 | 6/2005 | Kingsford |
| 2006/0047243 A1 | 3/2006 | Rosenberg |
| 2006/0068490 A1 | 3/2006 | Tang et al. |
| 2006/0142651 A1 | 6/2006 | Brister et al. |
| 2007/0004989 A1 | 1/2007 | Dhillon |
| 2007/0191696 A1 | 8/2007 | Mischler et al. |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1* | 4/2009 | Jina ..................... A61B 5/685 |
| | | 600/309 |
| 2009/0112125 A1 | 4/2009 | Tamir |
| 2009/0198215 A1 | 8/2009 | Chong et al. |
| 2009/0259176 A1 | 10/2009 | Yairi |
| 2010/0198107 A1 | 8/2010 | Groll et al. |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1* | 5/2011 | Chickering, III .. A61B 5/14514 |
| | | 600/573 |
| 2011/0105951 A1* | 5/2011 | Bernstein ......... A61B 5/150297 |
| | | 600/573 |
| 2011/0105952 A1* | 5/2011 | Bernstein ......... A61B 5/150412 |
| | | 600/573 |
| 2011/0125058 A1* | 5/2011 | Levinson ................ A61B 5/74 |
| | | 600/584 |
| 2011/0144463 A1 | 6/2011 | Pesach et al. |
| 2011/0172508 A1* | 7/2011 | Chickering, III .. A61B 5/15105 |
| | | 600/580 |
| 2011/0172510 A1* | 7/2011 | Chickering, III ...... A61B 5/157 |
| | | 604/173 |
| 2011/0198221 A1* | 8/2011 | Angelescu .......... F16K 99/0059 |
| | | 422/68.1 |
| 2011/0213335 A1 | 9/2011 | Burton et al. |
| 2011/0245635 A1 | 10/2011 | Fujiwara et al. |
| 2011/0257497 A1* | 10/2011 | Tamada ............. A61B 5/14514 |
| | | 600/365 |
| 2011/0288389 A9 | 11/2011 | Levinson et al. |
| 2012/0010529 A1* | 1/2012 | Chickering, III .. A61B 5/15105 |
| | | 600/583 |
| 2012/0016308 A1 | 1/2012 | Schott |
| 2012/0041338 A1 | 2/2012 | Chickering et al. |

(56) References Cited

U.S. PATENT DOCUMENTS

| | | |
|---|---|---|
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1* | 5/2012 | Brancazio .......... A61B 5/15107 600/576 |
| 2012/0259599 A1 | 10/2012 | Deck et al. |
| 2012/0271123 A1 | 10/2012 | Castle et al. |
| 2012/0271125 A1* | 10/2012 | Bernstein ......... A61B 5/150022 600/309 |
| 2012/0275955 A1* | 11/2012 | Haghgooie ...... A61B 5/150099 210/321.62 |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2013/0018279 A1 | 1/2013 | Plante et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1* | 10/2013 | Angelescu .............. E21B 47/02 73/54.01 |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1 | 10/2014 | Gelfand et al. |
| 2014/0309555 A1 | 10/2014 | Gelfand et al. |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1 | 7/2016 | Matsunami et al. |
| 2016/0256095 A1 | 9/2016 | Krasnow et al. |
| 2016/0262676 A1 | 9/2016 | Haghgooie et al. |
| 2016/0315123 A1 | 10/2016 | Kim et al. |
| 2016/0324506 A1 | 11/2016 | Tariyal et al. |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1 | 1/2017 | Todd et al. |
| 2017/0021117 A1 | 1/2017 | Howgill |
| 2017/0035337 A1 | 2/2017 | Wilkinson et al. |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna et al. |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1 | 3/2018 | Moga et al. |
| 2018/0103884 A1 | 4/2018 | Delamarche et al. |
| 2018/0126058 A1 | 5/2018 | David et al. |
| 2018/0132515 A1 | 5/2018 | Lawrence et al. |
| 2018/0132774 A1 | 5/2018 | Gonzalez-Zugasti et al. |
| 2018/0242890 A1* | 8/2018 | Chickering, III ......... A61B 5/150389 |
| 2018/0243543 A1 | 8/2018 | Baek et al. |
| 2018/0296148 A1 | 10/2018 | Gelfand et al. |
| 2018/0344631 A1 | 12/2018 | Zhang et al. |
| 2018/0369512 A1 | 12/2018 | Blatchford et al. |
| 2019/0000365 A1 | 1/2019 | Beyerlein et al. |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015582 A1* | 1/2019 | Naftalovitz ....... A61M 5/14248 |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1 | 5/2019 | Diebold et al. |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1 | 3/2020 | Berthier et al. |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1 | 8/2020 | Ivosevic et al. |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1 | 12/2021 | Weidemaier et al. |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0233117 A1 | 7/2022 | Lee et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |
| 2022/0330860 A1 | 10/2022 | Nawana |
| 2022/0361784 A1 | 11/2022 | Jordan et al. |
| 2023/0109881 A1 | 4/2023 | Nawana et al. |

FOREIGN PATENT DOCUMENTS

| | | |
|---|---|---|
| CN | 101296752 A | 10/2008 |
| EP | 0931507 A1 | 7/1999 |
| EP | 1769735 A1 | 4/2007 |
| EP | 2493537 A2 | 9/2012 |
| EP | 3513833 A1 | 7/2019 |

(56) References Cited

FOREIGN PATENT DOCUMENTS

| | | | |
|---|---|---|---|
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| JP | 2004024164 A | 1/2004 |
| KR | 101857300 B1 | 5/2018 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |

(56) References Cited

FOREIGN PATENT DOCUMENTS

| | | |
|---|---|---|
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016018892 A1 | 2/2016 |
| WO | 2016081843 A1 | 5/2016 |
| WO | 2016099986 A1 | 6/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion, PCT/US2022/029829, dated Nov. 23, 2022, 16 pages.
International Search Report and Written Opinion, PCT/US2022/046384, dated Jan. 5, 2023, 12 pages.
International Search Report and Written Opinion for PCT/US2022/046384 dated Jan. 5, 2023.
International Search Report and Written Opinion for PCT/US2022/048913 dated Feb. 21, 2023.
International Search Report and Written Opinion for PCT/US22/029829 dated Nov. 23, 2022.
International Search Report and Written Opinion, PCT/US2022/024607, dated Aug. 4, 2022, 17 pages.
Taiwan Office Action, TW111142334, dated May 18, 2023, 29 pages.
Taiwan Office Action, TW111142334, dated Dec. 12, 2023, 3 pages.
International Preliminary Report on Patentability for International Application No. PCT/US2022/024607 dated Oct. 12, 2023.
Written Opinion for International Application No. PCT/US2022/024607 issued Oct. 12, 2023.
International Preliminary Report of Patentability for International Application No. PCT/US2022/029829, Nov. 21, 2023.

* cited by examiner

DERMAL PATCH SYSTEM

CROSS REFERENCE TO RELATED APPLICATIONS

This application claim priority to and the benefit of U.S. Application No. 63/174,956, filed on Apr. 14, 2021 and U.S. Application No. 63/190,700, filed on May 19, 2021, the entire teachings of both of these applications are incorporated by reference herein.

TECHNICAL FIELD

The following relates to a dermal patch and more particularly to a dermal patch for storage of a physiological sample or detection of an analyte in a physiological sample.

BACKGROUND

Biomarkers are increasingly employed for diagnosis of various disease conditions as well as for assessing treatment protocols. Unfortunately, the invasive nature of drawing a blood sample from a patient can cause discomfort and may lead to less cooperation from a subject, especially children, and hence render obtaining a physiological sample that may contain a target biomarker difficult.

Some recently developed dermal patches allow for the detection target biomarkers, but typically suffer from a number of shortcomings, such as low sensitivity and/or specificity. Some dermal patches allow a user to obtain a physiological sample in order to send the obtained sample to a laboratory for further analysis that may not be able to be performed on the patch itself. Unfortunately, these dermal patches fail to provide a physiological sample preservation fluid within the dermal patch. This failure makes sample storage and preservation impractical thus rendering such at home sample collection solutions unsatisfactory.

SUMMARY

Aspects of the present disclosure address the above-referenced problems and/or others.

In one aspect, a system for collecting a physiological sample from a subject is disclosed. The system includes a dermal patch and an applicator that is configured for coupling to the dermal patch. The dermal patch may include a reservoir that stores a processing fluid and a sample collection chamber that receives the processing fluid and a physiological sample extracted from the subject. The applicator may include an actuating lever for activating the dermal patch to receive the physiological sample from the subject and directing the physiological sample into the sample collection chamber. In some embodiments, the dermal patch may also include a needle at for puncturing the subject's skin to draw the physiological sample. In other embodiments, at least a portion of the physiological sample is mixed with a processing fluid and at least a portion of the mixture is introduced into the collection chamber. The dermal patch may further include a detector. The detector may detect an analyte (e.g., a biomarker) in the mixture.

In some embodiments, the actuating lever is moveable between an undeployed position and a deployed position. When moved to the deployed position, the actuator draws the physiological sample from the subject and causes the physiological sample to travel to the collection reservoir. The applicator may include a pump. The pump creates a vacuum within the dermal patch when the actuating lever is moved to the deployed position. This vacuum draws the physiological sample into the collection chamber. In some embodiments, moving actuating lever from the undeployed position to the deployed position releases the processing fluid from the reservoir.

In another aspect, a system for collecting a physiological sample from a subject is disclosed, which includes a dermal patch and an applicator that is configured for coupling to the dermal patch. The dermal patch can include a reservoir configured for storing a processing fluid, a needle configured to puncture a subject's skin to allow drawing a physiological sample from the subject, and a sample collection chamber configured to receive the physiological sample and the processing reagent. In some embodiments, at least a portion of the physiological sample drawn from the subject is mixed with the processing fluid and at least a portion of the mixture is introduced into the collection chamber.

The applicator can include an actuating lever that is configured to move from an undeployed lever position to a deployed lever position, where the applicator is configured to cause the needle to puncture the subject's skin to allow drawing the physiological sample when the actuating lever is moved from the undeployed lever position to the deployed lever position.

In some embodiments, the applicator can be further configured to enable the transfer of the processing fluid and/or the physiological sample to the sample collection chamber when the actuating lever is moved from the undeployed lever position to the deployed lever position. In some embodiments, the patch can further include a mixing chamber that can receive the physiological sample drawn from the subject and the processing fluid and allow the mixing of the physiological sample with the processing fluid. The mixing chamber can be in turn in fluid communication with the sample collection chamber to allow transferring at least a portion of the mixture of the physiological sample and the processing fluid to the sample collection chamber.

In some embodiments, the transition of the actuating lever from its undeployed position to its deployed position can cause the movement of a plunger disposed in a chamber provided in the applicator for generating a vacuum in one or more fluid channels, in fluid communication with that chamber, so as to help with the transfer of the physiological sample drawn from the skin and/or the processing fluid via those fluidic channels into the collection chamber.

In some embodiments, the applicator can be removably coupled to the dermal patch. In other embodiments, the applicator and the dermal patch can be constructed as an integral unit.

A system according to the present teachings can be employed to extract and collect a variety of physiological samples. Some examples of such physiological sample include, without limitation, blood and interstitial liquid.

In some embodiment, the processing fluid can include one or more reagents for stabilizing the physiological sample drawn from the subject. By way of example and without limitation, in some embodiments, the reagents can include a buffer to establishing a desired pH and/or an anticoagulant for preventing, for example, a drawn blood sample from undergoing coagulation. Instead or in addition, the reagent can be heparin or a protease inhibitor.

In some embodiments, the dermal patch can include a sample storage element that is in fluid communication with the sample collection chamber (e.g., it can be disposed in the sample collection chamber) and is configured to store at least a portion of the physiological sample received in the sample collection chamber. For example, and without limitation, such a storage element can be a cellulose matrix, e.g., a filter paper, that can absorb at least a portion of the physiological sample received in the sample collection reservoir. In some embodiments, such a storage element can be removed from the dermal patch for analysis of the physiological sample stored on the storage element.

In some embodiments, an adhesive layer can be coupled to the dermal patch for attaching the dermal patch to a subject's skin. In some such embodiments, the dermal patch can include a first surface (herein also referred to as an upper surface) and a second opposed surface (herein also referred to as lower surface), where the applicator is configured to couple to at least portion of the first surface and the adhesive layer is coupled to the second surface. In some embodiments, a removable liner is coupled to the adhesive layer, where the liner can be removed for attaching the dermal patch onto a subject's skin.

The adhesive layer can have a variety of different shapes. For example, in some embodiments, the adhesive layer can be in the form of a strip that covers a perimeter of the second surface of the dermal patch. In other embodiments, the adhesive layer can be in the form of two substantially circular patches that can allow attaching the dermal patch onto the skin.

In some embodiments, the dermal patch includes a plurality of needles. By way of example, the number of needles can be in a range of about 2 to about 20, though other number of needles can be employed.

In some embodiments, an applicator according to the present teachings can be configured to create a vacuum within one or more fluidic channels in the dermal patch when an actuating lever is moved from the undeployed lever position to the deployed lever position, where the vacuum draws the physiological sample into the sample collection chamber.

By way of example, in some embodiments, the applicator can include a pump that is configured to be activated by an actuating lever of the applicator to create a vacuum in one or more fluidic channels of the dermal patch. By way of example, such a pump can include a plunger that is movably disposed within a chamber provided in the applicator. An actuating lever of the applicator can be coupled to the plunger to move the plunger from an inactive position to an active position, when the actuating lever is moved from an undeployed position to a deployed position, so as to apply a negative pressure to one or more fluidic channels within the dermal patch.

In some embodiments, the applicator can further include an element (herein also referred to as "reagent release element" or simply a "release element") that can cause the release of the processing fluid from the reservoir in which the processing fluid is contained, where the element is moved from an inactive position to an active position. In such embodiments, an actuating lever of the applicator can be operably coupled to the reagent release element such that the movement of the actuating lever from an undeployed position to a deployed position can transition can activate the reagent release element to cause the release of the processing fluid from its respective reservoir.

In some embodiments, the reservoir containing the processing fluid can include a frangible membrane for sealing the reservoir. In some embodiments, the release element can be configured (e.g., it can include a pointed tip) to puncture the frangible membrane when the release element is transitioned from its inactive state to its active state via the actuating lever so as to release the processing fluid contained in the reservoir for mixing with a physiological sample drawn from the subject.

In some embodiments, the applicator can also include a needle a needle activation element that is configured to cause the needle to puncture the subject's skin to draw the physiological sample when the actuating lever is moved from the undeployed lever position to the deployed lever position. For example, in some such embodiments, the needle activation element can be configured to move the needle from a retracted needle position to a deployed needle position in which the needle can puncture the subject's skin to draw the physiological sample.

In some embodiments, the needle activation element is disposed in a chamber (herein also referred to as a needle housing) provided in the applicator. In some such embodiments, an actuating lever of the applicator can be coupled to the needle activation element via a biasing element (e.g., a spring) that can cause the movement of the needle activation element from its retracted position to its deployed position.

In some embodiments, the dermal patch can include one or more physiological fluid channels that are in fluid communication with the needle housing and the sample collection chamber for transferring a physiological sample drawn from the subject to the sample collection chamber.

In some embodiments, the applicator is configured to create a vacuum, e.g., in a manner discussed herein, within the physiological fluid channel(s) to draw the physiological fluid through the punctured skin and transfer the drawn physiological sample to the sample collection chamber.

In some embodiments, a pump is incorporated in the applicator, which can be activated via an actuating lever of the applicator, to create a vacuum for drawing the physiological sample from the subject. As noted above, in some embodiments, the pump can include a plunger disposed in a pump chamber (herein also referred to as the pump housing) that is operably coupled to an actuating lever incorporated in the applicator such that the movement of the actuating lever from an undeployed position to a deployed position can activate the plunger to create the vacuum within the physiological fluid channel(s).

In one aspect, a diagnostic system is disclosed, which includes a dermal patch and an applicator that is configured for coupling to the dermal patch. The dermal patch can include a reservoir configured to store a processing fluid and a needle that is configured to puncture a subject's skin to draw a physiological sample from the subject. The dermal patch can further include a sensor that is configured to detect a target analyte in the physiological sample, e.g., in a sample generated via processing of the physiological sample with a processing fluid. The applicator can include an actuating lever that is configured to move from an undeployed lever position to a deployed lever position so as to activate the needle for puncturing the subject's skin in order to draw the physiological sample from the subject.

The applicator can be further configured to enable the transfer of the processed physiological sample to the sensor when the actuating lever is moved from the undeployed lever position to the deployed lever position. For example, as discussed in more detail below, the movement of the actuating lever between the undeployed and the deployed position can result in the activation of a pump incorporated in the applicator and in communication with at least one fluidic channel of the dermal patch for creating a vacuum in the fluidic channel for drawing the physiological sample into the fluidic channel.

The sensor can be configured to detect a target analyte when the target analyte is present in the processed physiological sample at a concentration level equal to greater than a threshold level, e.g., at a concentration equal or greater than a limit-of-detection of the sensor.

While in some embodiments the applicator can be removably coupled to the dermal patch, in other embodiments, the applicator and the dermal patch can be fabricated as a single integral unit.

By way of example, in some embodiments, the physiological sample can include blood while in other embodiments, the physiological sample can include the interstitial fluid.

A variety of processing reagents can be used in various embodiments of the dermal patch. For example, the processing fluid can help prepare the sample drawn from the subject for detection of a target analyte, if present in the sample, via the sensor. By way of example, the processing reagent(s) can be a buffer, one or more reagents needed for isothermal amplification of a target analyte. For example, the reagents can include the requisite primer(s) needed for isothermal amplification of the target analyte. By way of additional examples, in some cases, the processing reagent(s) can include reagents for stabilizing a drawn sample, e.g., a blood sample. In some embodiments, the processing reagent(s) can include an anti-coagulant (e.g., heparin) for inhibiting the coagulation of a blood sample drawn from a subject.

The sensor on board the patch can be configured to sense a variety of different analytes. For example, and without limitation, the sensor can be configured to detect one or more biomarkers. Some examples of biomarkers that can be detected by a dermal patch according to embodiments of the present teachings can include, without limitation, troponin, brain natriuretic peptide (BnP), myelin basic protein (MBP), ubiquitin carboxyl-terminal hydrolase isoenzyme L1 (UCHL-1), neuron-specific enolase (NSE), glial fibrillary acidic protein (GFAP), S100-B, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, or HbA1C.

In some embodiments, a target analyte can be a pathogen, e.g., a virus or a bacterium. In some embodiments, the sensor can be configured to detect such a pathogen via the detection of a protein or a genetic material thereof, e.g., segments of its DNA and/or RNA. In some embodiments, the sensors can be a lateral flow sensor that can be employed to detect a hormone.

A variety of sensors can be incorporated in a dermal patch according to the present teachings. Some examples of such sensors include, without limitation, an immunoassay sensor, an isothermal amplification detection system, a graphene-based sensor, an electrochemical sensor, and a chemical sensor, among others.

In some embodiments, an adhesive layer is coupled to the dermal patch to allow attaching the dermal patch to a subject's skin. For example, in some embodiments, the dermal patch can include a top surface that is configured for coupling to the applicator and a bottom surface to a portion of which an adhesive layer is coupled to allow attaching the dermal patch onto a subject's skin. The adhesive layer can have a variety of different shapes. For example, in some embodiments, the adhesive layer can be in the form a strip extending along a perimeter of the lower surface of the dermal patch. In other embodiments, the adhesive layer can be configured as two or more adhesive patches (e.g., circular patches) that can be employed to attach the dermal patch to the skin.

In some embodiments, the dermal patch can include a plurality of needles that are configured for puncturing the skin. By way of example, the number of the needles can be in a range of about 2 to about 20, though other number of needles can be employed.

In some embodiments, the sensor can include a visual indicator that indicates whether the sensor has detected the target analyte in the drawn physiological sample. In such embodiments, the dermal patch can include a window that allows viewing the visual indicator of the sensor.

In some embodiments, the applicator is configured to create a vacuum within the dermal patch when the actuating lever is moved from the undeployed lever position to the deployed lever position such that the created vacuum draws the physiological sample via the subject's punctured skin to the sensor.

By way of example, in some such embodiments, the applicator includes a pump for creating the vacuum. In some such embodiments, the pump can include a plunger that is disposed in a plunger housing provided in the applicator and the actuating lever can be configured to move the plunger from an inactive position to an active position when the actuating lever is moved from the undeployed lever position to the deployed lever position. The transition of the plunger from its inactive position to its active position can result in the application of a negative pressure to one or more fluidic channels in the dermal patch for drawing a physiological sample through the punctured skin and/or causing the flow of the processing fluid from the fluid reservoir, e.g., to a chamber in which the processing fluid and the drawn physiological sample are mixed.

In some embodiments, the applicator can further include a release element configured to cause the release of the processing fluid from the reservoir in which the processing fluid is stored when the actuating lever is moved from the undeployed lever position to the deployed lever position. By way of example, the release element can be configured to puncture a frangible membrane that seals the fluid reservoir, thereby allowing the release of the processing fluid from the reservoir. By way of example, in some such embodiments, the release element can include a pointed tip that is configured to puncture the frangible membrane.

The applicator can further include a needle activation element that is configured to cause one or more needles incorporated in the dermal patch to be activated for puncturing the subject's skin to allow drawing a physiological sample. More specifically, an actuating lever of the applicator can be operably coupled to the needle activation element so as to move the needle activation element from an inactive state to an active state when the actuating lever is moved from an undeployed position to a deployed position. For example, in some embodiments, the needle activation element can be disposed in a chamber provided in the housing and can be coupled to a biasing element (e.g., a spring), such that the needle activation element can be moved, via the actuating lever, from a retracted position in which the needle activation element is fully disposed in its chamber to an extended position in which it activates the needle in the dermal patch to puncture a subject's skin.

In some embodiments, the dermal patch can further include a sample collection chamber (herein also referred to as a mixing chamber), that can receive a physiological sample drawn from a subject as well as the processing fluid released from the processing fluid reservoir. The drawn physiological sample and the processing fluid can be mixed in the sample collection chamber to generate a processed sample. Further, the sample collection chamber is in fluid communication with the sensor such that the processed sample can be delivered to the sensor for analysis.

The dermal patch can further include a physiological fluidic channel that is configured to receive a physiological sample drawn through a subject's punctured skin and to deliver the received physiological sample to the sample collection chamber.

The applicator can be further configured to create a vacuum within the physiological fluidic channel to allow drawing the physiological sample into the physiological fluid channel and to transfer the drawn physiological sample via the fluidic channel to the sample collection chamber. In some such embodiments, a pump incorporated in the applicator can create the vacuum in the physiological fluidic channel. By way of example, such a pump can include a plunger that is movably disposed within a pump housing (chamber) provided in the applicator so as to move from an inactive position (herein also referred to as an inactive state) to an active position (herein also referred to as an active state). For example, the plunger can be operably coupled to an actuating lever provided in the applicator such that the movement of the actuating lever from an undeployed position to a deployed position causes the movement of the plunger from the inactive position to the active position in which a vacuum can be created in one or more fluidic channels in the dermal patch, such as the aforementioned physiological fluidic channel. In some embodiments, a biasing element (e.g., a spring) can help moving the plunger between its active and inactive positions.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description when taken in conjunction with the accompanying drawings in which.

DETAILED DESCRIPTION

Figure 1:
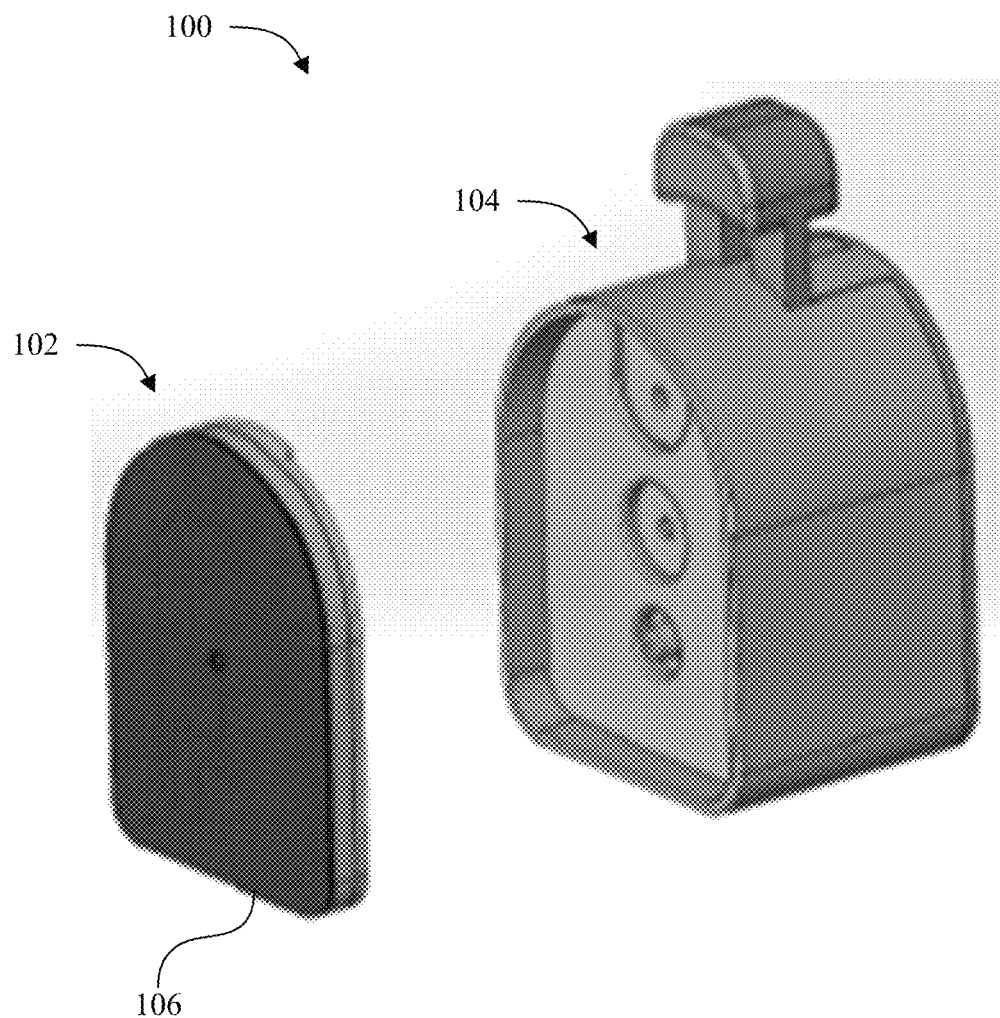
FIG. 1 depicts a dermal patch and an applicator in accordance with an exemplary embodiment.

The present disclosure generally relates to a system and method that may be utilized to collect and store a physiological sample (e.g., blood, interstitial fluid, etc.) or detect a target analyte in a collected physiological sample.

In some embodiments, a dermal patch that is used to collect a physiological sample may include a processing fluid (e.g., reagent, buffer, anticoagulant, etc.). The processing fluid may be suitable for preserving the physiological sample. Providing a system with a dermal patch that includes a processing sample allows for the collection and preservation of a physiological sample within the dermal patch. Such a system may allow a user of the system to collect a physiological sample themselves at home and store the collected sample for further testing.

In other embodiments, a dermal patch that is used to detect a target analyte (e.g., a biomarker) in a physiological sample includes a needle to draw the physiological sample, a processing fluid, and a sensor that detects a target analyte. The processing fluid may be suitable for amplification of a target analyte (e.g., a primer). Providing a system with a dermal patch that includes a needle, a processing fluid, and a sensor allows for the drawing of a physiological sample and the detection of a target analyte within the dermal patch. Such a system may have enhanced sensitivity and/or specificity over other dermal patches that detect a target analyte.

Various terms are used herein in accordance with their ordinary meanings in the art, unless indicated otherwise. The term "about," as used herein, denotes a deviation of at most 10% relative to a numerical value. The term "substantially," as used herein, refers to a deviation, if any, of at most 10% from a complete state and/or condition. The terms "needle" and "microneedle" are used herein to broadly refer to an element that can provide a passageway, or facilitate the production of a passageway, for collecting a physiological sample, such as a blood or an interstitial fluid sample through a patient's skin, e.g., via puncturing the subject's skin. The term "transparent," as used herein, indicates that light can substantially pass through an object (e.g., a window) to allow visualization of a material disposed behind the object. For example, in some embodiments, a transparent object allows the passage of at least 70%, or at least 80%, or at least 90%, of the visible light therethrough.

With reference to FIG. 1, a system 100 is disclosed in accordance with an exemplary embodiment. The system 100 includes a dermal patch 102 and an applicator 104. In some embodiments, the dermal patch 102 is removably coupled to the applicator 104. In other embodiments, the dermal patch 102 is integrally coupled to the applicator 104. While in this embodiment, the dermal patch 102 and the applicator 104 are formed of two portions that are coupled to one another, in other embodiments the dermal patch 102 and the applicator 104 may be formed as a single unit.

The dermal patch 102 and the applicator 104 may be formed from polymeric materials including, but not limited to, polymeric materials, e.g., polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, at least a portion of the dermal patch 102 or the applicator 104 may be formed poly(dimethylsiloxane) (PDMS) to allow visibility of at least a portion of the components disposed with the dermal patch 102 or the applicator 104.

Figure 2:
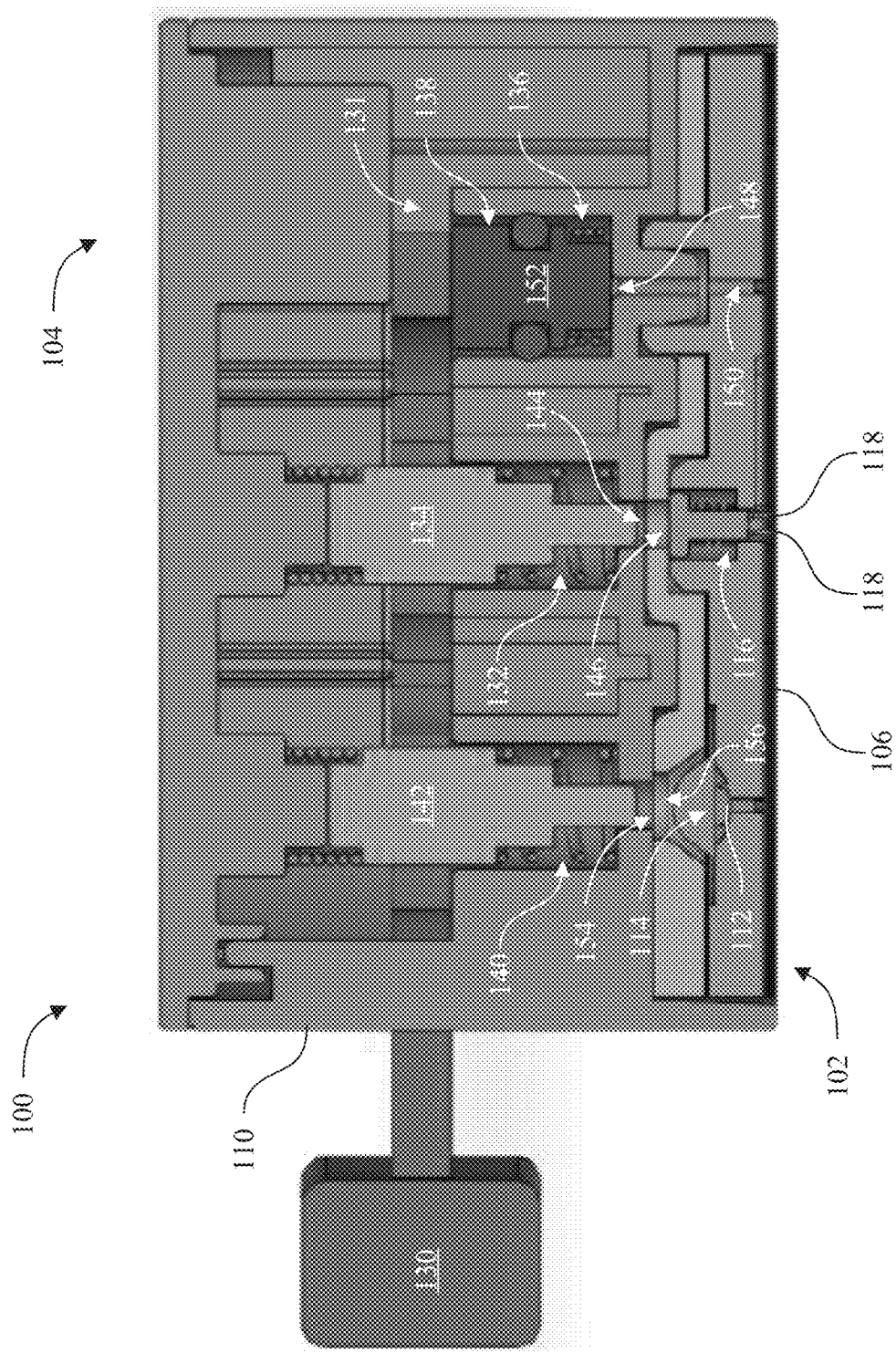
FIG. 2 is a cross sectional view of a dermal patch coupled to an applicator wherein an actuating lever of the applicator is in an undeployed position in accordance with an exemplary embodiment.

With reference to FIG. 2, the dermal patch 102 and the applicator 104 are further depicted in accordance with an exemplary embodiment wherein the dermal patch 102 is coupled to the applicator 104. As depicted in FIG. 2, the dermal patch includes an adhesive layer 106 for attaching the dermal patch 102 to a subject. Briefly turning to FIG. 3, another embodiment of the dermal patch 102 is further depicted. In this embodiment, the adhesive layer 106 includes a first circular patch 106A and a second circular patch 106B. The first circular patch 106A and the second circular patch 106B are connected to the dermal patch 102 via first connector 108A and a second connector 108B respectively. In this embodiment, when the dermal patch 102 is worn on an arm of a subject, the first connector 108A and the second connector 108B wrap around opposite sides the subject's arm thereby allowing the first circular patch 106A and the second circular patch 106B to adhere to opposite sides of the subject's arm.

Returning to FIGS. 2 and 4, the dermal patch 102 further includes a housing 110. The housing 110 includes a reservoir 112, a frangible membrane 114, a needle housing 116 including two needles 118, and a sample collection chamber 120 that receives the processing fluid and a physiological sample.

The reservoir 112 stores a processing fluid. In some embodiments, the processing fluid is suitable for preserving a physiological sample including, but not limited to, an anti-coagulant (e.g., heparin, a protease inhibitor, etc.). Furthermore, the frangible membrane 114 seals the processing fluid within the reservoir 112. In many embodiments, the reservoir 112 is pre-filled with the requisite processing fluid such that the dermal patch 102 can be used without a need to fill the reservoir 112 with the processing fluid at the point of care. In other words, a user can utilize the dermal patch 102 with all the requisite processing fluid on board. This feature provides distinct advantages in that it ensures consumer safety and reduces, and preferably eliminates, the risk of error. In other words, in many embodiments a dermal patch 102 contains all the necessary sample processing fluid for its intended use.

The needles 118 are configured to puncture a subject's skin and penetrate through a subject's stratum corneum and at least a portion of the epidermal layer to draw a physiological fluid (e.g., capillary blood and/or interstitial fluid). In some embodiments, the needles 118 may be movable between a retracted position and a deployed position. In the deployed position, the needles 118 are exposed for puncturing the skin. The needle housing 116 includes an opening that is in concert with an opening of the adhesive layer 106 which allows the needles 118 to contact the subject's skin when moved from a retracted to a deployed position. While FIG. 2 depicts the dermal patch 102 as include two needles 118, in other embodiments the dermal patch 102 may include a different number of needles 118 (e.g., 1, 4, 10, etc.).

Figure 4:
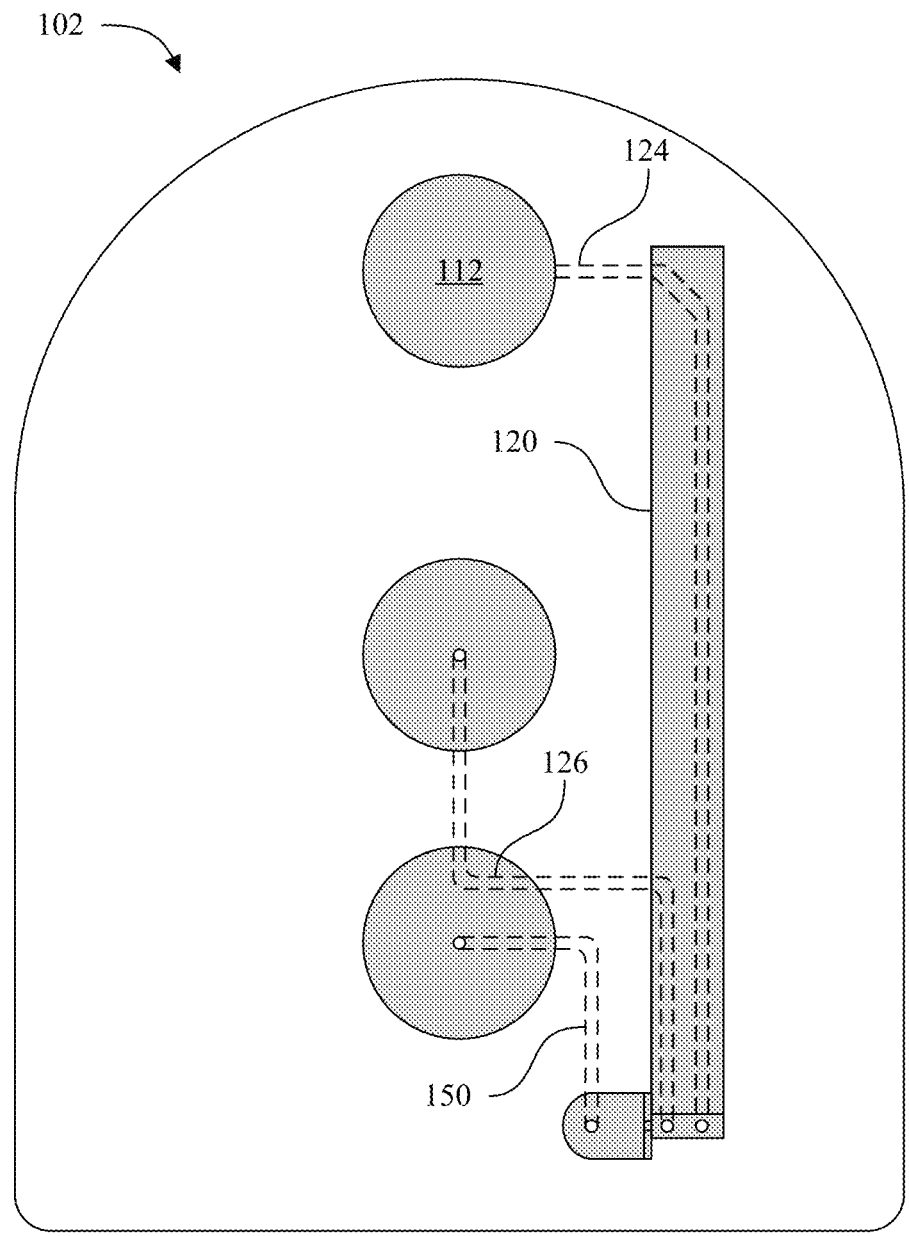
FIG. 4 depicts a dermal patch in accordance with an exemplary embodiment.

With reference to FIG. 4, the reservoir 112 is in fluid communication with the sample collection chamber 120 via a processing fluid channel 124. The processing fluid channel 124 is configured to carry the processing fluid from the reservoir 112 to the sample collection chamber 120. The processing fluid channel 124 includes an inlet positioned beneath and in fluid communication with the reservoir 112. The inlet receives the processing fluid when the processing fluid is released from the reservoir 112. The processing fluid channel 124 further includes an outlet positioned beneath and in fluid communication with the sample collection chamber 120. Processing fluid exits the processing fluid channel 124 and enters the sample collection chamber 120 via the outlet.

The needle housing 116 is in fluid communication with the sample collection chamber 120 via a physiological fluid channel 126. The physiological fluid channel 126 is configured to carry the physiological sample from the needle housing 116 to the sample collection chamber 120. The physiological fluid channel 126 includes an inlet positioned beneath and in fluid communication with the needle housing 116. The inlet receives the physiological fluid when the needles 118 draw the physiological sample. The physiological fluid channel 126 further includes an outlet positioned beneath and in fluid communication with the sample collection chamber 120. The physiological fluid exits the physiological fluid channel 126 and enters the sample collection chamber 120 via the outlet.

When the processing fluid and the physiological sample enter the collection chamber 120, the processing fluid mixes and interacts with the physiological sample to form a processed physiological sample. In this embodiment, the processed physiological sample is suitable for storage. The processed physiological sample is stored within the sample collection chamber 120 and may be further analyzed at a later time.

Figure 5:
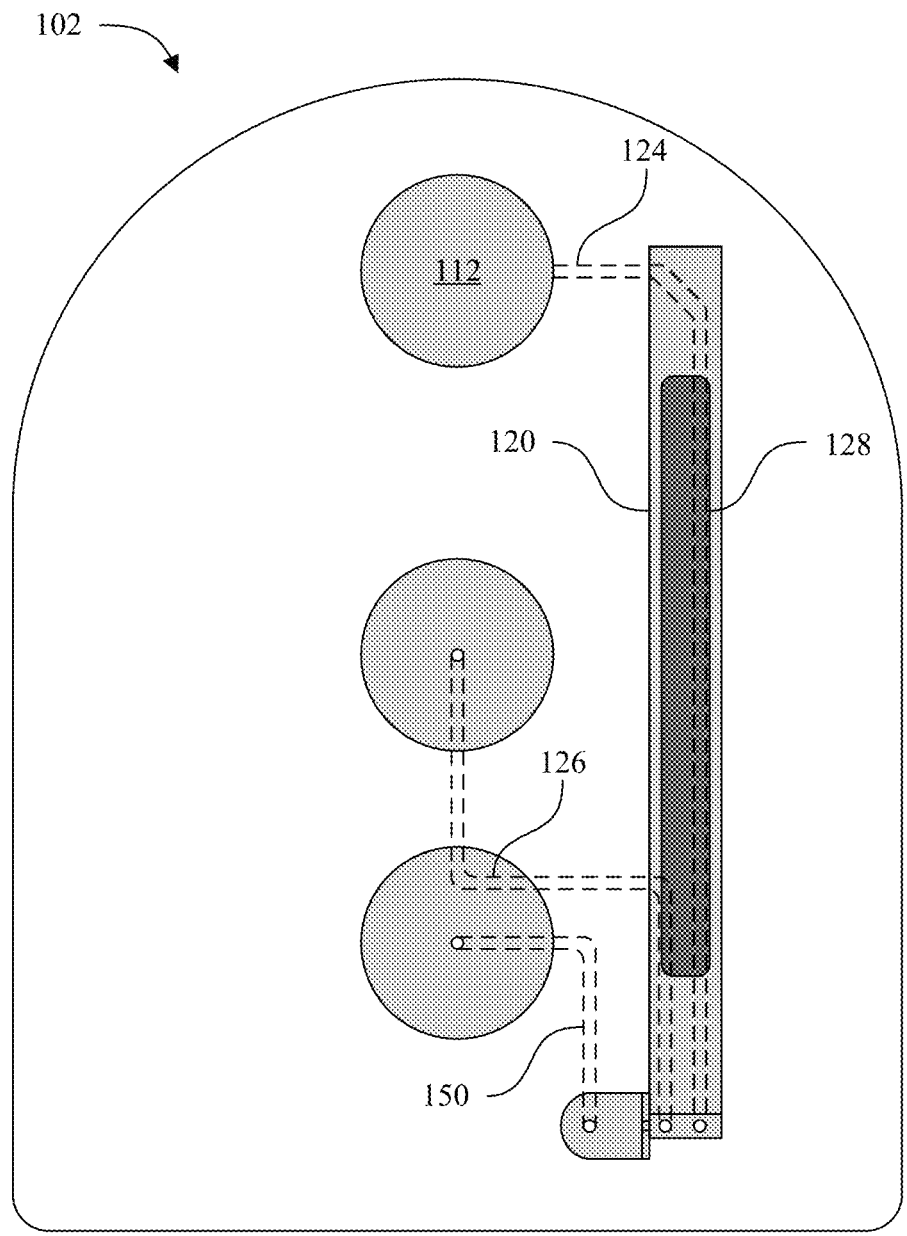
FIG. 5 depicts another dermal patch in accordance with an exemplary embodiment.

FIG. 5 depicts an embodiment of the dermal patch 102, wherein the dermal patch 102 includes a storage element 128. The storage element 128 is in fluid communication with the sample collection chamber 120 and configured to store a processed physiological sample received in the sample collection chamber 120. The storage element 128 may include, but is not limited to, a filter paper matrix.

Figure 6:
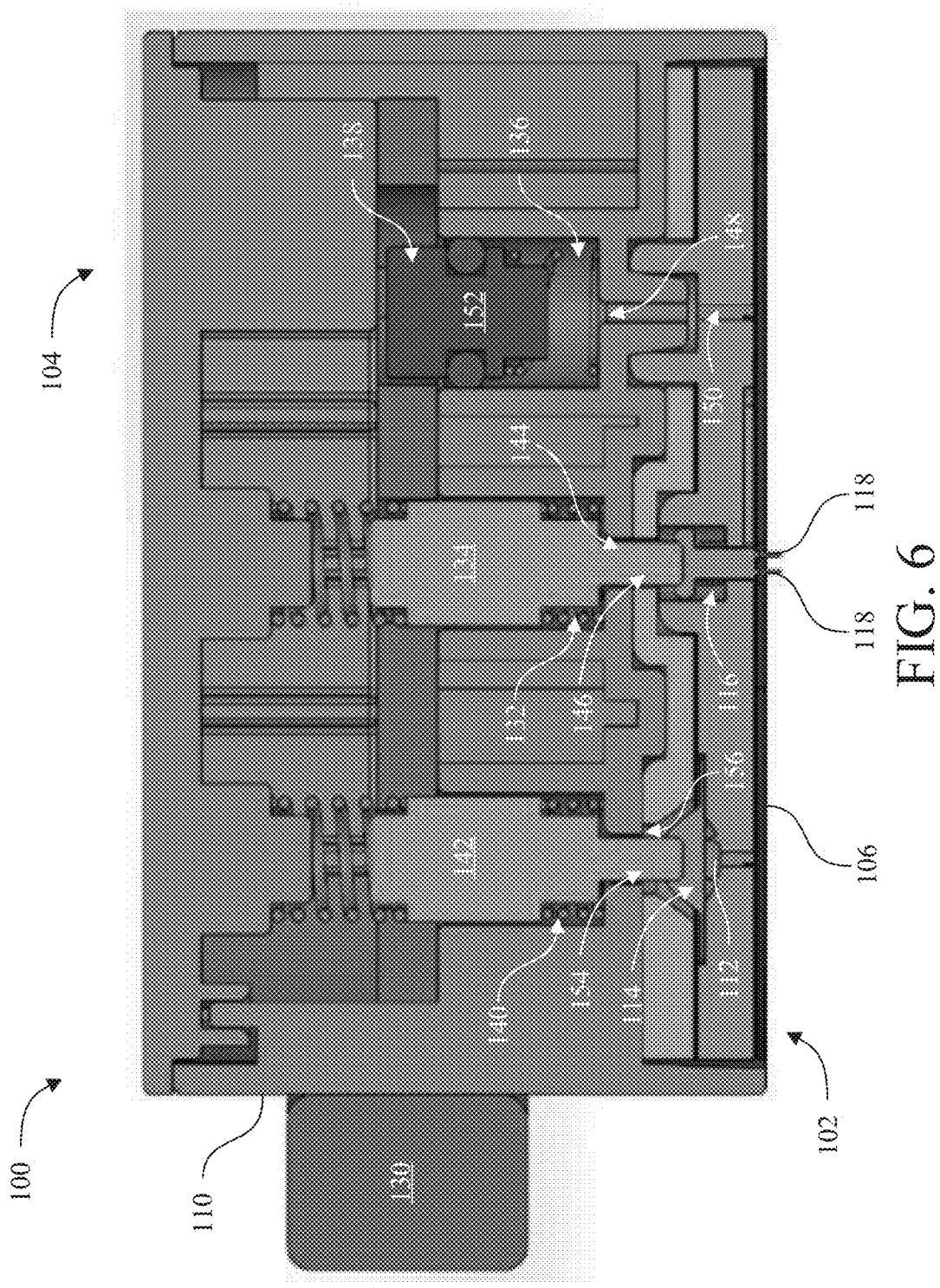
FIG. 6 is a cross sectional view of a dermal patch coupled to an applicator wherein an actuating lever of the applicator is in a deployed position in accordance with an exemplary embodiment.

Returning to FIG. 2, the applicator 104 includes an actuating lever 130. As will be discussed in further detail herein, the actuating lever 130 is moveable between an undeployed position (FIG. 2) and a deployed position (FIG. 6) within a chamber 131 of the housing 110. The applicator 104 further includes a needle activation element housing 132 that includes a needle activation element 134, a pump housing 136 that includes a pump 138, and a release element housing 140 that includes a release element 142.

The needle activation element 134 is moveable between an undeployed position (FIG. 2) to a deployed position (FIG. 6) within the needle activation element housing 132. The actuating lever 130 moves the needle activation element 134 when the actuating lever 130 is moved from the undeployed position to the deployed position. The needle activation element housing 132 includes an opening 144 that is in concert with an opening 146 of the needle housing 116. When moved, the needle activation element 134 moves through the openings 144 and 146 and causes the needles 118 to move from the retracted position to the deployed position which causes the needles 118 to puncture the subject's skin to draw the physiological sample.

The pump housing 136 includes an opening 148 that is in fluid communication with a vacuum channel 150. As depicted in FIG. 4, the vacuum channel 150 is in fluid communication with the sample collection chamber 120. As a result, the vacuum channel 150 is also in fluid communication with the needle housing 116. The pump 138 includes a plunger 152 that is moveable between an inactive position (FIG. 2) and an active position (FIG. 6) within the pump hosing 136. The actuating lever 130 moves the plunger 152 when the actuating lever 130 is moved from the undeployed position to the deployed position. The pump 138 is configured to create a vacuum within the dermal patch 102. More specifically, the pump 138 is configured to create vacuum within the vacuum channel 150 by evacuating the vacuum channel 150 to a pressure below the atmospheric pressure when the plunger 152 is moved to the active position. This vacuum draws the physiological sample through the physiological fluid channel 126 and into the sample collection chamber 120.

The release element 142 is moveable between an undeployed position (FIG. 2) to a deployed position (FIG. 6) within the release element housing 140. The actuating lever 130 moves the release element 142 when the actuating lever 130 is moved from the undeployed position to the deployed position. The release element housing 140 includes an opening 154 that is in concert with an opening 156 of the dermal patch 102 that is vertically above the reservoir 112. When moved, the release element 142 moves through the openings 154 and 156 and causes the release element to release the processing fluid thereby and causes the processing fluid to flow out of the reservoir 112. When released, the processing fluid enters the processing fluid channel 126 and flows to the sample collection chamber 120. In embodiments wherein the dermal patch 102 includes the frangible membrane 114, the release element 142 breaks the frangible membrane to release the processing fluid. In some embodiments, the release element 142 punctures the frangible membrane to release the processing fluid.

Figure 7:
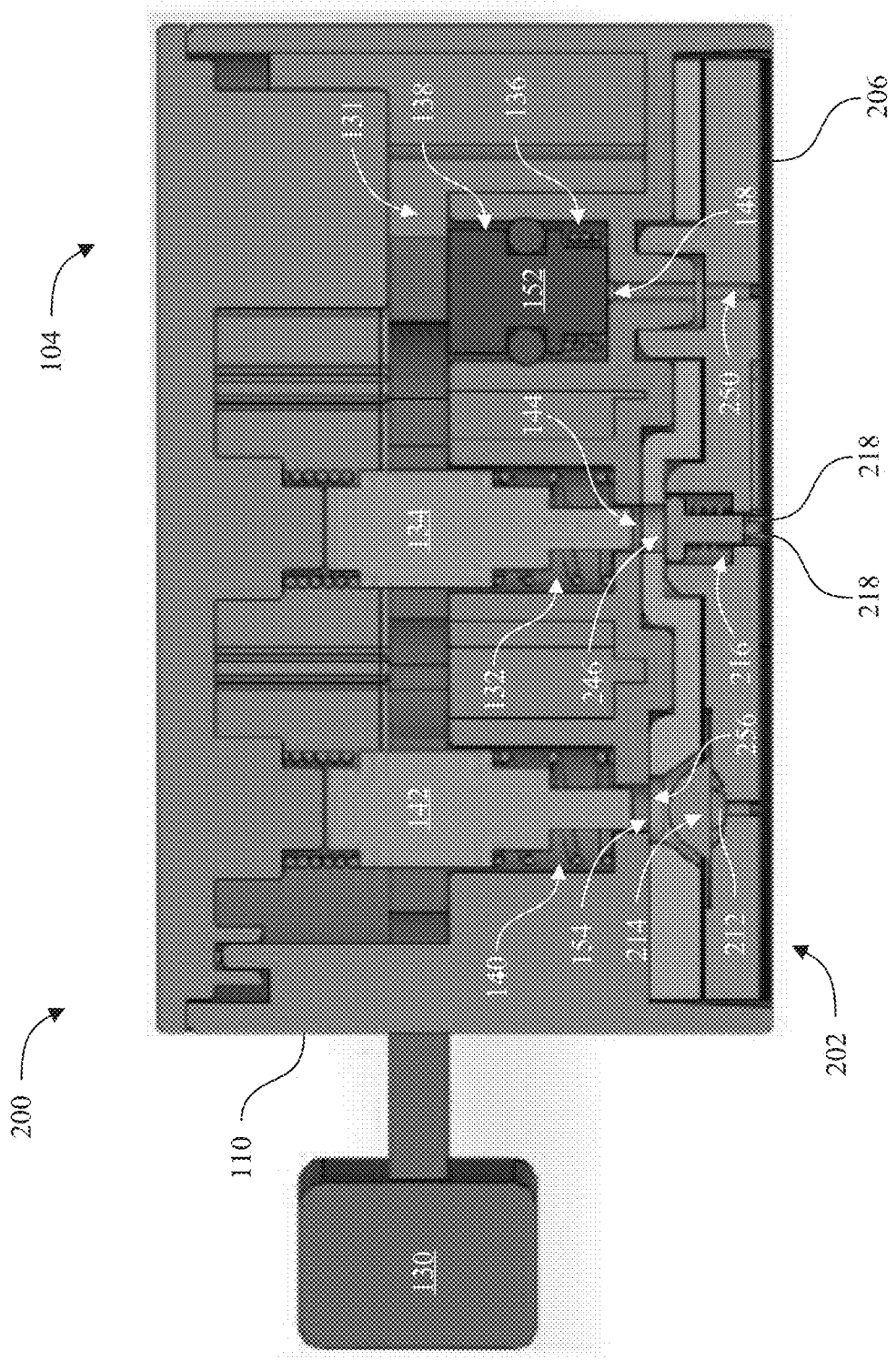
FIG. 7 is a cross sectional view of a dermal patch coupled to an applicator wherein an actuating lever of the applicator is in an undeployed position in accordance with an exemplary embodiment.
Figure 8:
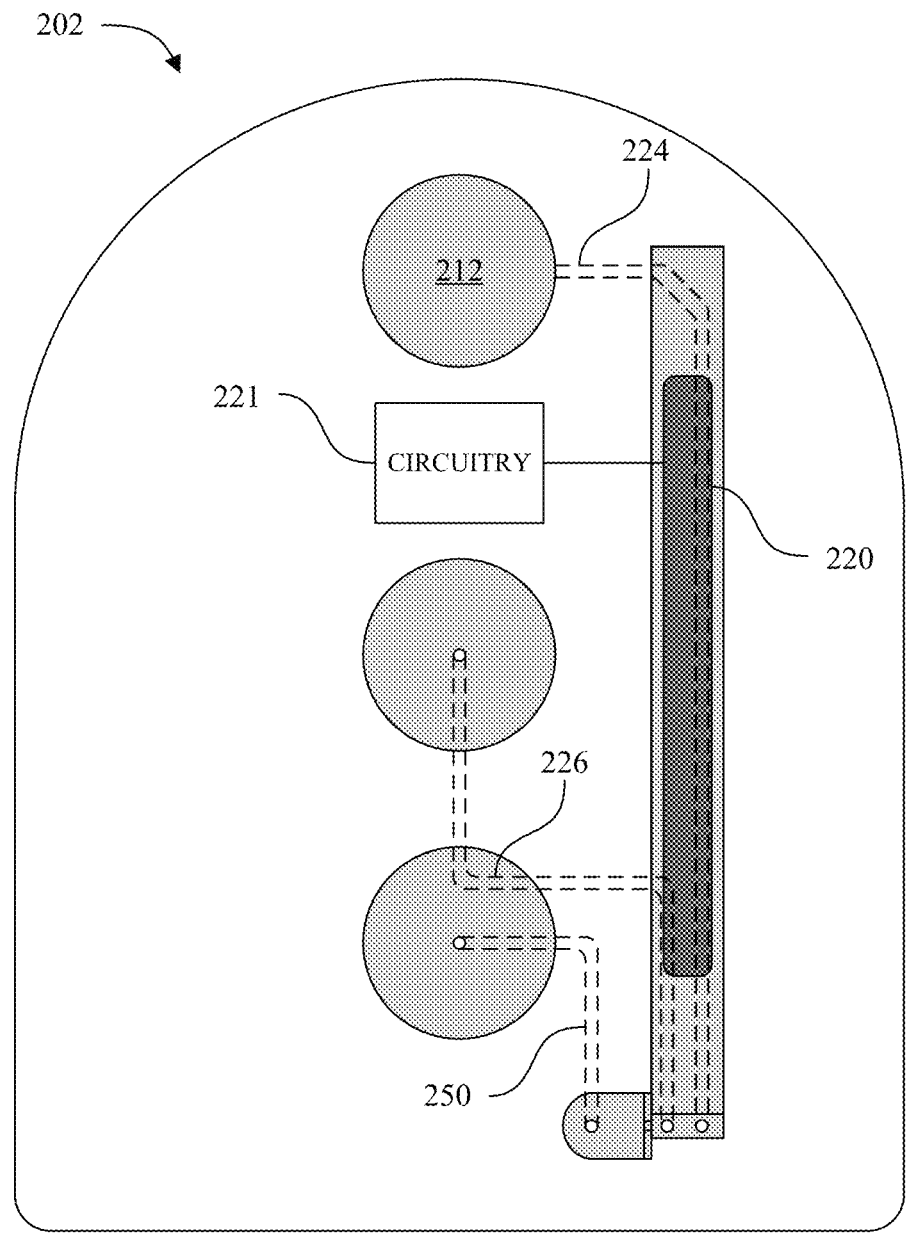
FIG. 8 depicts another dermal patch in accordance with an exemplary embodiment.

With reference to FIGS. 7 and 8, a system 200 is disclosed in accordance with an exemplary embodiment. The system 200 includes a dermal patch 202 and the applicator 104. In some embodiments, the dermal patch 202 is removably coupled to the applicator 104. In other embodiments, the dermal patch 202 is integrally coupled to the applicator 104. The dermal patch 202 and the applicator 104 may be formed from polymeric materials as previously discussed herein.

Figure 3:
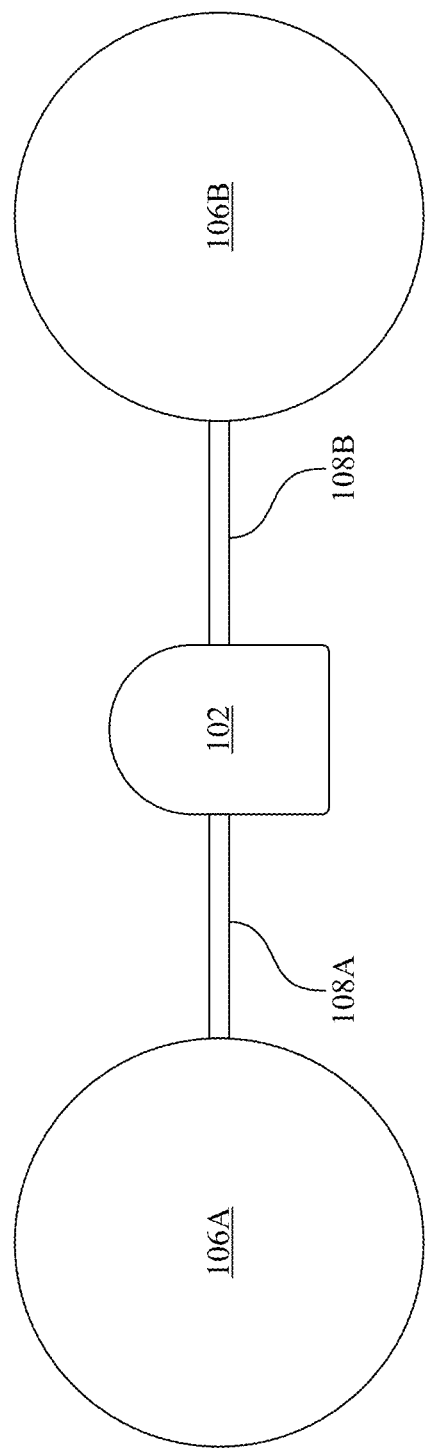
FIG. 3 depicts a dermal patch with two circular adhesive pads in accordance with an exemplary embodiment.

The dermal patch 202 includes an adhesive layer 206 for attaching the dermal patch 202 to a subject. In some embodiments the adhesive layer 206 includes two circular patches as depicted in FIG. 3. The dermal also includes a housing 210. The housing 210 includes a reservoir 212, a frangible membrane 214, a needle housing 216 including two needles 218, and a sensor 220 that receives the processing fluid and a physiological sample.

The reservoir 212 stores a processing fluid. In some embodiments, the processing fluid is suitable for isothermal amplification a target analyte, including but not limited to, a primer. In many embodiments, the reservoir 212 is pre-filled with the requisite processing fluid such that the dermal patch 202 can be used without a need to fill the reservoir 212 with the processing fluid at the point of care as previously discussed herein.

The needles 218 are configured to puncture a subject's skin and penetrate through a subject's skin to draw a physiological sample and may be movable between a retracted position and a deployed position as previously discussed herein. The needle housing 216 includes an opening 222 that is in concert with an opening of the adhesive layer 106 which allows the needles 218 to contact the subject's skin when moved from a retracted to a deployed position. While FIG. 7 depicts the dermal patch 202 as include two needles 218, in other embodiments the dermal patch 202 may include a different number of needles 218 (e.g., 1, 4, 10, etc.).

With reference to FIG. 8, the reservoir 212 is in fluid communication with the sensor 220 via a processing fluid channel 224. The processing fluid channel 224 is configured to carry the processing fluid from the reservoir 212 to the sensor 220. The processing fluid channel 224 includes an inlet positioned beneath and in fluid communication with the reservoir 212. The inlet receives the processing fluid when the processing fluid is released from the reservoir 212. The processing fluid channel 224 further includes an outlet positioned beneath and in fluid communication with the sensor 220. Processing fluid exits the processing fluid channel 224 and enters the sensor 220 via the outlet.

The needle housing 216 is in fluid communication with the sensor 220 via a physiological fluid channel 226. The physiological fluid channel 226 is configured to carry the physiological sample from the needle housing 216 to the sensor 220. The physiological fluid channel 226 includes an inlet positioned beneath and in fluid communication with the needle housing 216. The inlet receives the physiological fluid when the needles 218 draw the physiological sample. The physiological fluid channel 226 further includes an outlet positioned beneath and in fluid communication with the sensor 220. The physiological fluid exits the physiological fluid channel 226 and enters the sensor 220 via the outlet.

When the processing fluid and the physiological sample enter the collection chamber 220, the processing fluid mixes and interacts with the physiological sample to form a processed physiological sample. The sensor 220 may then detect a target analyte within the processed physiological sample. In some embodiments, the sensor 220 may detect a target analyte when the target analyte is equal to or greater than a threshold (e.g., a limit-of detection (LOD)). In other embodiments, the sensor may be calibrated to determine a quantitative level of the target analyte (e.g., the concentration of the target analyte in the collected sample).

The sensor 220 may be a variety of different sensors capable of detecting a target analyte (e.g., a graphene-based detector, a chemical detector, a lateral flow sensor, a DNA sequencing sensor, an RNA sequencing sensor, etc.). Furthermore, the sensor 220 may be a passive sensor or an active sensor and may provide chromatographic or "photovisual," or digital readouts (e.g., a colorimetric sensor, an immunoassay sensor including lateral flow sensors, isothermal amplification detection systems, etc.). In some embodiments in which a colorimetric sensor is employed, at least a portion of the dermal patch may include a transparent portion to allow the visualization of the sensor 220.

As previously discussed herein, the sensor 220 is in fluid communication with the processing fluid channel 224 and the physiological fluid channel 226 for coming into contact with at least a portion of the processed physiological sample and to generate one or more signals in response to the detection of a target analyte, when present in the sample. By way of example, the sensor 220 can be coupled to processing fluid channel 224 and the physiological fluid channel 226 via a sealed opening. Other suitable means for interrogating a sample may also be employed. By way of example, in some cases, the interrogation of a processed physiological sample may be achieved without the need for direct contact between a sensor 220 and the sample (e.g., optical techniques, such as fluorescent and/or Raman techniques).

In some embodiments, the dermal patch 202 may include circuitry 221 that is in communication with the sensor 220 of the dermal patch 202 and receives one or more signals (e.g., detection signals) generated by the sensor 220. The circuitry 221 may be configured to process the signals to determine the presence of a target analyte in the processed physiological sample and optionally quantify the level of the target analyte, when present in the processed physiological sample. In addition or instead, the signals generated by the sensor 220 may be processed the circuitry 221 or an external device to quantify the level of the target analyte detected in the sample. By way of example, such quantification may be implemented using previously-generated calibration data in a manner known in the art as informed by the present teachings. In these embodiments, the circuitry The circuitry 221 may be implemented using the techniques known in the art. By way of example, the circuitry may include at least one memory module for storing the signals generated by the sensor 220. The circuitry 221 may be configured to process the stored signals, e.g., detection signals, generated by different types of sensor 220. The circuitry 221 may also include a communication module to allow communication between the circuitry 221 and an external electronic device. Such an external electronic device may be a mobile electronic device. By way of example, in some embodiments, a variety of wireless communication protocols may be used for transmitting data from the circuitry to the external electronic device. Some examples of such wireless communication protocols may include Bluetooth, Wi-Fi, and BTLE protocol for establishing a communication link between the patch and the electronic device.

The circuitry 221 may be implemented on a printed circuit board (PCB), that is in communication with the sensor 220. The connection between the circuitry 221 and the sensor 220 may be established via any of a wired or wireless protocol. In some embodiments, the circuitry 221 and/or the sensor 220 can be supplied with power via an on-board power supply, e.g., a battery, incorporated, e.g., on the circuitry. Alternatively, in some implementations, the circuitry and/or the sensor can be provided with power via an external device, e.g., a wearable device. Such transfer of power from an external device may be achieved using techniques known in the art, such as inductive coupling between two elements (e.g., two coils) provided in the dermal patch and the external device.

The circuitry 221 may include an application-specific integrated circuit (ASIC) that is configured for processing the signal data generated by the sensor 220. The circuitry 221 can further include one or more memory modules for storing, for example, instructions for processing the data generated by the sensor 220.

While FIG. 8 depicts the dermal patch 202 as including the circuitry 221, in some embodiments the circuitry 221 may be omitted. In these embodiments, the sensor 220 may detect the target analyte without any circuitry 221 needed (e.g., a lateral flow assay).

In some embodiments, a target analyte may be a pathogen, e.g., a virus or a bacterium. In some embodiments, the sensor 220 can be configured to detect such a pathogen via the detection of a protein or a genetic material thereof, e.g., segments of its DNA and/or RNA. In other embodiments, the sensor 220 may be a lateral flow sensor that can be employed to detect a hormone. In other embodiments, the target analyte may be a biomarker, e.g., a biomarker that may be indicative of a disease condition, e.g., organ damage. In some embodiments, the biomarker may be indicative of a traumatic brain injury (TBI), including a mild traumatic brain injury. Some example of such a biomarker include, without limitation, any of myelin basic protein (MBP), ubiquitin carboxyl-terminal hydrolase isoenzyme L1 (UCHL-1), neuron-specific enolase (NSE), glial fibrillary acidic protein (GFAP), and S100-B.

In other embodiments, the dermal patch may be configured for the detection of other biomarkers, such as troponin, brain natriuretic peptide (BnP), and HbA 1C. Other examples include, but are not limited to, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, HbA1C.

Further, in some embodiments, the sensor 220 may be configured to detect one or more biomarkers for diagnosis of brain damage, such as traumatic brain injury (TBI). Some examples of such biomarkers include, but are not limited to, myelin basic protein (MBP), ubiquitin carboxyl-terminal hydrolase isoenzyme L1 (UCHL-1), neuron-specific enolase (NSE), glial fibrillary acidic protein (GFAP), and S100-B.

By way of example, the sensor 220 may be configured to measure levels of the protein biomarkers UCHL-1 and GFAP, which are released from the brain into blood within 12 hours of head injury. The levels of these two proteins measured by the sensor 220 according to the present disclosure after a mild TBI can help identify those patients that may have intracranial lesions.

In one embodiment a target analyte may be detected the sensor 220 when the sensor 220 is a graphene-based sensor that includes a graphene layer that is functionalized with a moiety (e.g., an antibody, an aptamer, an oligonucleotide, etc.) that exhibits specific binding to that target analyte (e.g., a protein, a DNA segment) such that upon binding of the target analyte to that moiety an electrical property of the underlying graphene layer changes, thus indicating the presence of the target analyte in the sample. Some examples of suitable graphene-based sensors are disclosed in U.S. Pat. Nos. 10,782,285, 10,401,352, 9,664,674, as well as published U.S. Patent Applications Nos. 20200011860, and 20210102937, each of which is herein incorporated by reference in their entirety.

By way of example, the detection of a target analyte may be achieved by using a graphene-based sensor and/or an electrochemical sensor that is functionalized with a probe, such as an antibody and/or aptamer, which exhibits specific binding to that target analyte, though other sensing technologies may also be utilized.

In another embodiment, the sensor 220 may be an electrochemical sensor that can function in a faradaic or non-faradaic mode to detect a target analyte of interest. For example, such an electrochemical sensor may include a working electrode, a reference electrode and a counter electrodes. By way of example, in some embodiments, the reference electrode may be functionalized with a moiety that exhibits specific binding to a target analyte such that upon binding of that target analyte, when present in the sample, to the moiety, a change in the current through the circuit may be detected.

In some embodiments, at least one serum-separation element is associated with the sensor 220 for receiving blood and separating a serum/plasma component of the blood for introduction into said at least one of the sensing units.

The serum-separating element may include a fibrous element that is configured to capture one or more cellular components of the blood so as to separate a plasma/serum component of the blood for analysis. For example, in such embodiments, the serum component can be introduced in a respective sensing unit for analysis, e.g., for detection and optionally quantification of one or more biomarkers and/or other analytes. In some embodiments, the serum-separating element is a nitrocellulose strip. The use of such a fibrous element, and in particular a nitrocellulose strip, can allow sufficient fractionation of the blood to enhance significantly the sensitivity/specificity of detection of analytes (e.g., biomarkers) in the separated serum, especially using a graphene-based sensor. In other words, although the use of a nitrocellulose strip in a patch according to some embodiments may not result in fractionation of the whole blood sample with the same degree of separation quality that is achievable via traditional fractionation methods, such as differential centrifugation; nonetheless, the applicant has discovered that the use of such a nitrocellulose strip in embodiments of the dermal patch can significantly enhance the sensitivity/specificity for the detection of a variety of analytes (e.g., biomarkers) using a variety of detectors, such as graphene-based detectors, relative to the use of a whole blood sample for such detection. In some embodiments, wherein the sensor 220 is a graphene sensor, the nitrocellulose strip may be coupled to the sensor 220 and the sensor 220 may detect the target analyte via the nitrocellulose strip.

Furthermore, the serum-separation element may include at least one fibrous membrane configured to capture at least a portion of one or more cellular components of the received blood, thereby separating a serum (or a plasma) component of the blood.

In some embodiments, the separated plasma or the serum component can still include some cellular elements. Even without having a level of fractionation that is achieved via traditional methods, such as differential centrifugation, the separated serum component can be utilized to achieve an enhanced detection sensitivity/specificity relative to using whole blood for detecting, and optionally quantifying, a variety of target analytes in a drawn blood sample. Some examples of such target analytes may include, without limitation, a biomarker, such as troponin, brain natriuretic peptide (BnP), or other biomarkers including those disclosed herein.

The separated serum component may include any of a plurality of red blood cells and/or a plurality of white blood cells and/or platelets. However, the concentration of such cellular components in the separated serum component can be less than that in the whole blood by a factor in a range of about 2 to about 1000, though lower concentrations can also be achieved.

Figure 9:
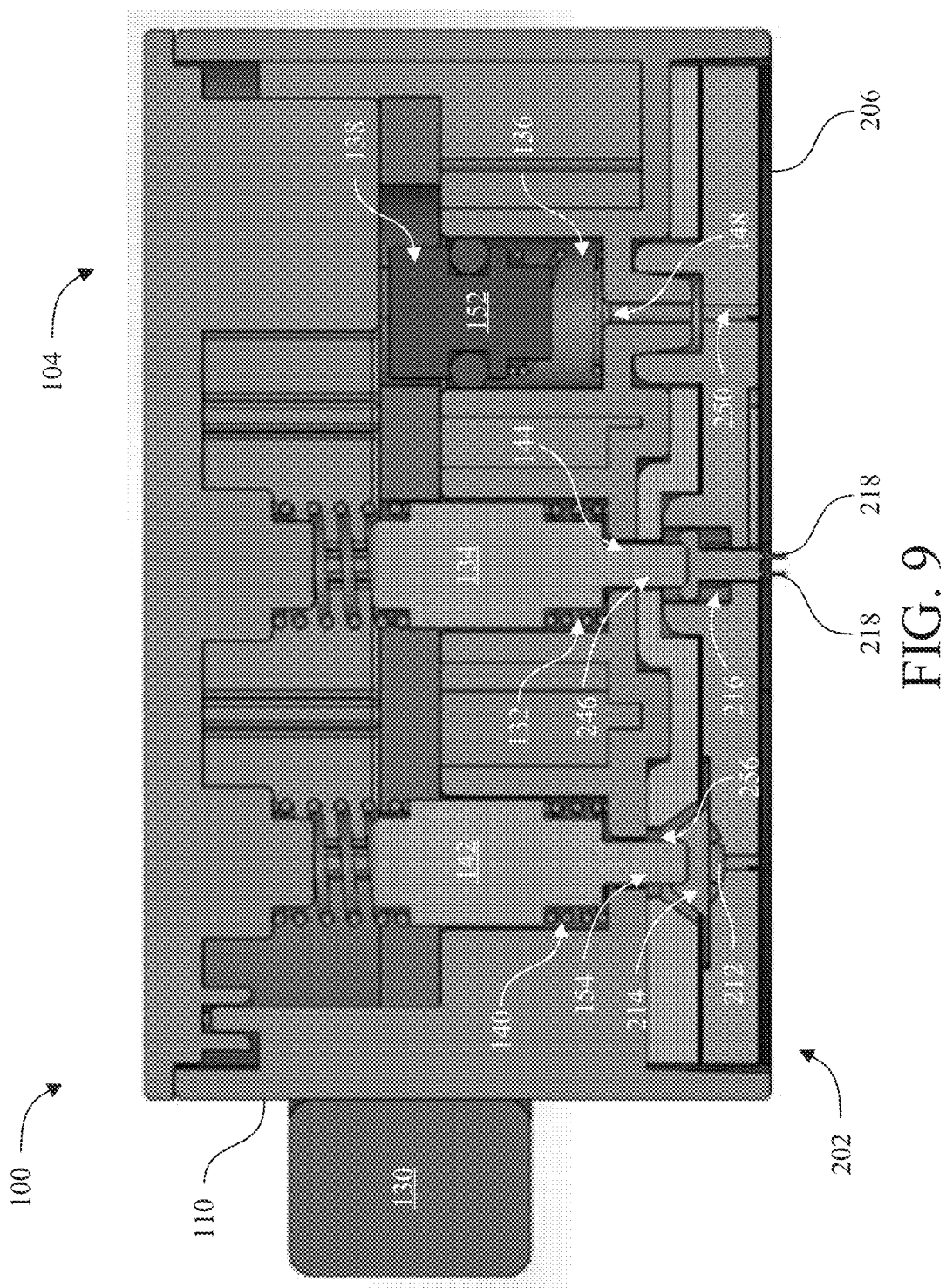
FIG. 9 is a cross sectional view of a dermal patch coupled to an applicator wherein an actuating lever of the applicator is in a deployed position in accordance with an exemplary embodiment.

Returning to FIG. 7, the applicator 104 includes an actuating lever 130. As previously discussed herein, the actuating lever 130 is moveable between an undeployed position (FIG. 7) and a deployed position (FIG. 9) within a chamber 131 of the housing 110.

The needle activation element 134 is moveable between an undeployed position (FIG. 7) to a deployed position (FIG. 9) within the needle activation element housing 132 as previously discussed herein. The actuating lever 130 moves the needle activation element 134 when the actuating lever 130 is moved from the undeployed position to the deployed position. When moved, the needle activation element 134 moves through the openings 144 and 246 and causes the needles 218 to move from the retracted position to the deployed position which causes the needles 218 to puncture the subject's skin to draw the physiological sample.

In this embodiment, the opening 148 of the pump housing 136 is in fluid communication with a vacuum channel 250 of the dermal patch 200. As depicted in FIG. 7, the vacuum channel 250 is in fluid communication with the sensor 220. As a result, the vacuum channel 250 is also in fluid communication with the needle housing 216.

The actuating lever 130 moves the plunger 152 when the actuating lever 130 is moved from the undeployed position to the deployed position and the pump 238 is configured to create a vacuum within the dermal patch 202 as previously discussed herein. More specifically, the pump 238 is configured to create vacuum within the vacuum channel 250 when the plunger 152 is moved to the active position. This vacuum draws the physiological sample through the physiological fluid channel 226 and to the sensor 220.

The release element 142 is moveable between an undeployed position (FIG. 7) to a deployed position (FIG. 9) as previously discussed herein. In this embodiment the opening 154 that is in concert with an opening 256 of the dermal patch 202 that is vertically above the reservoir 212. When moved, the release element 142 moves through the openings 154 and 256 and causes the release element to release the processing fluid thereby and causes the processing fluid to flow out of the reservoir 212 as. When released, the processing fluid enters the processing fluid channel 226 and flows to the sensor 220. In embodiments wherein the dermal patch 202 includes the frangible membrane 214, the release element 142 breaks the frangible membrane to release the processing fluid. In some embodiments, the release element 142 punctures the frangible membrane to release the processing fluid.

Figure 10:
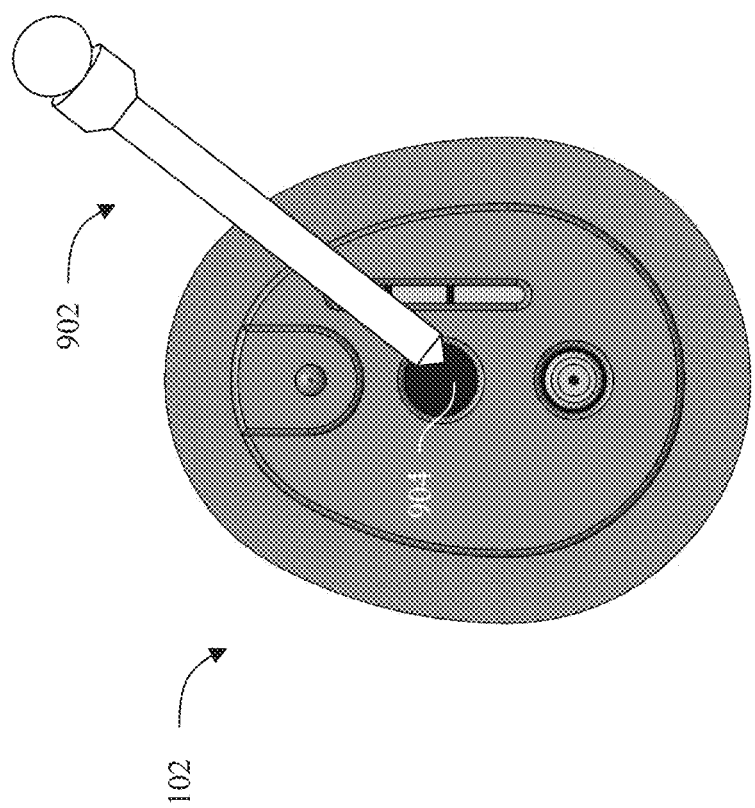
FIG. 10 depicts a lancet and a dermal patch in accordance with an exemplary embodiment.

In some embodiments, rather than utilizing an applicator, a dermal patch according to the present teachings can be activated by a user using an implement, e.g., a lancet enclosed in a trocar. By way of example, with reference to FIG. 10, a dermal patch 102 according to the present teachings can be coupled to a patient's upper arm, e.g., via an elastic band having a hook-and-loop fastener that can apply a moderate pressure to the subject's arm. A lancet 902 can be used to penetrate through a septum 904 of the dermal patch 104 so as to puncture the skin so as to allow blood to enter the dermal patch under the influence of the pressure applied to the subject's arm. The lancet 902 may include a pressure or a vacuum bulb that a user may push to promote the flow of the physiological sample to the sample collection chamber 902.

Subsequently, the same trocar having a lancet can be used to cause the release of the processing fluid (or at least a portion thereof) from the fluid reservoir for mixing with the drawn blood sample. For example, the lancet may retracted into the trocar and the tip of the trocar can be pressure on a flexible membrane sealing the fluid reservoir to cause the fluid to be released from the fluid reservoir, e.g., in a manner discussed above in connection with the applicator.

In other embodiments, the needles 118, after drawing the physiological sample, may apply positive pressure to push the drawn physiological sample to the sample collection chamber 120. In these embodiments, the pump 138 and the vacuum channel 150 may be omitted.

While the invention has been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A dermal patch system for collecting a physiological sample from a subject comprising:
   a housing that includes:
   a needle configured to move between an undeployed position and a deployed position, wherein the needle is configured to draw a physiological sample from the subject in the deployed position,
   a reservoir that stores a processing fluid,
   a chamber configured to receive the processing fluid and the drawn physiological sample, and
   a lever configured to move between an undeployed position and a deployed position such that a transition of the lever from the undeployed position to the deployed position releases the processing fluid from the reservoir and moves the needle to the deployed position.

2. The system of claim 1, wherein the transition of the lever from the undeployed position to the deployed position draws the released processing fluid and the drawn physiological sample to the chamber.

3. The system of claim 1, wherein the needle and the lever are separable.

4. The system of claim 1, wherein the physiological sample comprises any of blood and interstitial fluid.

5. The system of claim 1, wherein the processing fluid includes a reagent or a buffer.

6. The system of claim 1, wherein the processing fluid includes an anti-coagulant.

7. The system of claim 1, wherein the processing fluid includes heparin or a protease inhibitor.

8. The system of claim 1, further comprising a storage element in fluid communication with the sample collection chamber and configured to store the physiological sample received in the sample collection chamber.

9. The system of claim 8, wherein the storage element includes a filter paper matrix.

10. The system of claim 1, comprising an adhesive layer configured for attaching the dermal patch to the subject's skin.

11. The system of claim 2, further comprising:
    a first fluidic channel configured to carry the processing fluid to the chamber.

12. The system of claim 11, further comprising:
    a second fluidic channel configured to carry the drawn physiological sample to the chamber.

13. The system of claim 12, wherein the transition of the lever from the undeployed position to the deployed position creates a vacuum within the first fluidic channel and the second fluidic channel that draws the processing fluid and the drawn physiological sample to the chamber.

14. The system of claim 13, further comprising:
    a pump configured to create the vacuum.

15. The system of claim 14, wherein the pump includes a plunger and the lever is configured to move the plunger to create the vacuum when the lever is moved from the undeployed position to the deployed position.

16. The system of claim 15, further comprising:
    a release element configured to release the processing fluid from the reservoir when the lever is moved from the undeployed position to the deployed position.

17. The system of claim 16, wherein the reservoir comprises a frangible member and the release element is configured to rupture the frangible membrane to release the processing fluid stored therein.

18. A system for collecting a physiological sample, comprising:
    a dermal patch configured to attach to the skin of the subject, and including:
       a needle configured to move between an undeployed position and a deployed position, wherein the needle is configured to draw a physiological sample from the subject in the deployed position, and
       a storage element configured to absorb the drawn physiological sample, and
    an applicator configured to removably couple to the dermal patch, and including:
       a lever configured to move between an undeployed position and a deployed position such that a transition of the lever from the undeployed position to the deployed position causes the needle to move to the deployed position to draw the physiological sample and facilitate delivery of the drawn physiological sample to the storage element.

19. The system of claim 18, wherein said storage element includes a filter paper matrix.

20. The system of claim 18, further comprising a sample collection chamber that retains the storage element.

21. The system of claim 20, further comprising a physiological fluid channel configured to carry the physiological sample to the sample collection chamber.

* * * * *